United States Patent [19]

Christena

[11] 4,289,587

[45] Sep. 15, 1981

[54] STABILIZATION OF CHLORINATED PHENOLS

[75] Inventor: Ray C. Christena, Wichita, Kans.

[73] Assignee: Vulcan Materials Company, Birmingham, Ala.

[21] Appl. No.: 144,880

[22] Filed: Apr. 29, 1980

[51] Int. Cl.³ .......................... B01D 3/34; C07C 37/74
[52] U.S. Cl. ........................................... 203/6; 203/58; 203/60; 203/61; 203/86; 568/702; 568/776
[58] Field of Search ...................... 203/6, 7, 38, 61, 60, 203/58, 86; 568/702, 701, 755, 776

[56] References Cited

U.S. PATENT DOCUMENTS

| | | | |
|---|---|---|---|
| 2,806,888 | 9/1957 | Davis | 568/701 |
| 2,965,539 | 12/1960 | Loper et al. | 568/702 |
| 3,403,188 | 9/1968 | Schlichting et al. | 568/702 |
| 3,637,772 | 1/1972 | Klaui et al. | 568/701 |
| 3,852,161 | 12/1974 | Yoshimine et al. | 203/6 |
| 3,871,970 | 3/1975 | Nienburg et al. | 203/6 |
| 4,016,047 | 4/1977 | Christena | 203/6 |
| 4,142,943 | 3/1979 | Kobel et al. | 568/755 |

*Primary Examiner*—Wilbur L. Bascomb, Jr.
*Attorney, Agent, or Firm*—Burns, Doane, Swecker & Mathis

[57] ABSTRACT

Chlorinated phenols, e.g. pentachlorophenol, are stabilized against degradation, including degradation to chlorinated dibenzo-p-dioxins, caused by heat and other adverse conditions, by combining with them stabilizing amounts of at least one stabilizer selected from the group consisting of high-boiling epoxides and epoxidized oils, drying oils, unsaturated fatty acids and unsaturated esters of fatty acids.

20 Claims, No Drawings

STABILIZATION OF CHLORINATED PHENOLS

BACKGROUND OF THE INVENTION

For some time it has been recognized that chlorinated phenols, and especially polychlorinated phenols, are susceptible to degradation by heat. Such degradation may be accelerated by contact with or exposure to scale, rust, metals, light, air, and chemical impurities.

Much has been written about the negative effects of this degradation, the focus being on the undesirability of color formation in the polychlorinated phenols. Pentachlorophenol is a well-known wood preservative agent; degraded pentachlorophenol exhibits a characteristic dark reddish or brownish color which causes discoloration in wood products to which it is applied. Thus, U.S. Pat. Nos. 3,909,365 and 4,016,047 disclose certain free radical-acting substances that may be added to polychlorinated phenols such as pentachlorophenol to act as scavengers for the color-forming impurities thereby permitting removal of the impurities from the chlorinated phenols during distillation. The compounds disclosed include certain phenols, hydroquinones, sulfur compounds, alkyl phosphites, amines, and other specific agents including zinc dust, and sodium borohydride. These additives are said to react with the color-forming impurities in the polychlorinated phenols to render them separable on distillation.

Concern has recently begun to focus on certain impurities such as the various chlorinated dibenzo-p-dioxins, hereinafter referred to by their common name as "chlorodioxins", which may be toxic to humans, possibly even in the low concentrations, e.g., about 2,000 parts per million, present in technical grade pentachlorophenol. These chlorodioxin impurities, especially octachlorodibenzo-p-dioxin and some hexachlorodibenzo-p-dioxin, are apparently formed when phenol is chlorinated to produce pentachlorophenol, and also subsequently when pentachlorophenol is heated for any reason, e.g., to be processed into a commercially salable form or in ultimately being used in the molten state. If the health hazard of the chlorodioxins is established then it will be necessary to remove them or reduce their concentration in pentachlorophenol to a safe level (i.e., below about 100 p.p.m.), and to maintain such a low level of contamination throughout subsequent processing, particularly where the pentachlorophenol is heated.

Other degradation products commonly found in pentachlorophenol that have been identified include isomers of chlorinated diphenyl ethers, chlorinated benzenes and isomers of chlorinated dibenzofurans. These compounds may be sources of additional health hazards.

This toxicity problem becomes particularly difficult to avoid when it is necessary to heat impure pentachlorophenol, such as technical grade pentachlorophenol, above its boiling point in order to purify it by distillation. Pentachlorophenol is a high-boiling solid, pure pentachlorophenol having a melting point of 190° to 191° C. After distillation, which is commonly conducted under reduced pressure at a temperature between about 185° and about 235° C., the distillation product must ordinarily be kept hot so as to keep it liquid until it can be converted into the desired final form, e.g. blocks, pellets, flakes, prills, etc. Alternatively the distillation product may be cooled and collected as a solid to be remelted later to convert it into the desired final form.

Purified pentachlorophenol can be safely heated in glass or stainless steel at 204° C., its remelt temperature, for at least three hours without an increase in chlorodioxins. However, at 232° C. (450° F.), purified pentachlorophenol cannot be heated even one hour in stainless steel or Monel metal without build-up of chlorodioxins or other decomposition products.

Numerous compounds and compositions have been disclosed in the prior art as stabilizers for polychlorinated phenols. In particular, previously disclosed compounds and compositions include: a mixture comprising an aromatic o-hydroxycarboxylic acid, a polycarboxylic acid and an ester of a phosphorus acid, such as an alkyl or aryl phosphite (U.S. Pat. No. 3,403,186); a hydroxybenzaldehyde such as salicylaldehyde (U.S. Pat. No. 3,770,835, U.S. Pat. No. 3,852,160 and U.S. Pat. No. 3,852,161); a high boiling amine or alkanolamine (U.S. Pat. No. 3,816,268); and hydroxyl- or polyhydroxyl-containing organic compounds including sugars, polyhydric alcohols, polyglycols and ethers of polyglycols (U.S. Pat. No. 4,142,943).

OBJECTS AND SUMMARY OF THE INVENTION

It is an object of this invention to provide a novel class of stabilizers that greatly reduce the degradation of chlorinated phenols, particularly pentachlorophenol, resulting from exposure of such chlorinated phenols to one or more known accelerators of degradation, including, but not limited to, heat, scale, rust, glass, metals, light, air, and chemical impurities.

It is another object to provide an improved pentachlorophenol composition comprising a stabilizing amount of at least one stabilizer selected from the group consisting of high-boiling epoxides and epoxidized oils, drying oils and other unsaturated esters of fatty acids, unsaturated fatty acids themselves, and mixtures of two or more such compounds or materials, which is characterized by having a substantially increased resistance to heat-induced chemical degradation and containing no more than a permissible small amount of chlorodioxins.

It is still another object to provide an improved process for purifying pentachlorophenol by distillation, wherein the distillation is carried out in the presence of a stabilizing amount of a stabilizer selected from the group consisting of high-boiling epoxides and epoxidized oils, drying oils, and other unsaturated esters of fatty acids, unsaturated fatty acids themselves, and mixtures of two or more such compounds or materials.

It is a further object to provide an improved process wherein pentachlorophenol that has been distilled and condensed is maintained in the molten state for a period of time, or, after solidification, is remelted by heating above its melting point for some reason, for example, for further processing into a final salable form, e.g. blocks, flakes, prills, beads, pellets, etc. and wherein the improvement comprises adding to the molten material or to the solid product to be remelted a stabilizing amount of at least one stabilizer selected from the group consisting of high-boiling epoxides and epoxidized oils, drying oils, unsaturated fatty acids, and unsaturated esters of fatty acids and mixtures thereof.

In essence, the invention comprises the stabilization of pentachlorophenol against chemical degradation, and particularly against heat-induced degradation, by adding to pentachlorophenol a stabilizing amount of at least one stabilizer selected from the group consisting of high-boiling epoxides and epoxidized oils, drying oils, unsaturated fatty acids, and unsaturated esters of fatty acids and mixtures thereof. The invention likewise comprises the stabilized pentachlorophenol compositions so produced.

In the absence of a contrary indication, all proportions and percentages of materials are expressed in this specification on a weight basis.

DESCRIPTION OF PREFERRED EMBODIMENTS

The invention may advantageously be employed to stabilize any chlorinated phenol containing 1 to 5 chlorine atoms per molecule, e.g., monochlorophenol, 2,4-dichlorophenol, 2,4,6-trichlorophenol or tetrachlorophenol, but it is particularly applicable to the stabilization of pentachlorophenol. Pentachlorophenol is commonly used in the preservation of wood and as a general herbicide.

Pentachlorophenol, to which this invention is especially applicable, may be produced in any suitable manner. Generally, pentachlorophenol is produced by the chlorination of phenol or by hydrolysis of hexachlorobenzene. Although either method is acceptable and both methods are known in the art, production of pentachlorophenol by the chlorination of phenol is preferred.

The phenol starting material, which may be chlorinated to form the chlorinated phenols, may be produced by the decomposition of cumene hydroperoxide or by sulfonation of benzene.

Chlorination may be conducted in any convenient manner known. Chlorination processes are shown, for example, in U.S. Pat. Nos. 2,131,259 and 2,947,790.

Typically, in these known processes the phenol starting material is reacted at a temperature at the start of the chlorination in the range of 65° C. to 130° C. (preferably about 100° C. to 110° C.) and is held at this temperature until the melting point of the product is 95° C. and about 3 atoms of chlorine are combined as determined by analysis, at which time catalyst is added and the temperature is progressively increased to maintain a preferred differential temperature of 10° C. over the product melting point. Chlorination of the phenol is continued until 5 chlorine atoms are added.

The chlorination process is carried out at substantially atmospheric pressure for a time of from about 5 to about 15 hours. The chlorination reaction may be carried out in the liquid phase in the absence of any added solvents and in the presence of aluminum chloride catalyst. The catalyst concentration in these known chlorination processes is maintained below 0.0085 mol of anhydrous aluminum chloride per mol of phenol, preferably not more than 0.075 mol and not less than 0.004 mol of anhydrous aluminum chloride per mol of phenol. The initial chlorination up to where 2 to 2.7 atoms of chlorine are combined per mol of phenol may be carried out in the absence of catalyst.

Pentachlorophenol production by hydrolysis of hexachlorobenzene is also well known and is shown, for example, in U.S. Pat. Nos. 2,107,650 and 2,812,366.

Generally, all of the above-noted processes yield technical grade pentachlorophenol, which is a commonly available commercial product. Technical grade pentachlorophenol is a generally brownish-colored solid that contains from about 86 to 94 percent pentachlorophenol, about 2 to 10 percent tetrachlorophenol and up to about 4 percent of other compounds, most of which are unidentified. As noted before, technical grade pentachlorophenol also commonly contains about 1800 to 2400 p.p.m. of octachlorodibenzo-p-dioxin.

According to this invention, technical grade pentachlorophenol can be separated from its impurities by distillation in the presence of certain stabilizers. The pentachlorophenol is vaporized and recovered as pure pentachlorophenol by condensation of the vapor while the impurities remain behind unvaporized in the still bottoms.

The stabilizers that find use in the present invention can be categorized under two general headings: first, epoxidized vegetable or animal oils and other epoxides; and second, free unsaturated fatty acids, their triglycerides, e.g., natural drying oils, other esters of such fatty acids, e.g., synthetic drying oils formed by the esterification of unsaturated fatty acids, as well as synthetic drying oils obtained by the polymerization of a diolefin such as butadiene-1,3 or of mixtures comprising same, which may be further treated with maleic anhydride or other polar compounds as disclosed, for instance, in U.S. Pat. Nos. 2,652,342; 2,683,162; 2,762,851; or the like. Preferably, such stabilizers have an atmospheric boiling point above 150° C., and most preferably about 190° C., i.e., above the melting point of pentachlorophenol, although low-boiling compounds when suitably supplied can be satisfactory even if they are distilled over with the pentachlorophenol.

Representative of the first category are, for instance, phenyl glycidyl ether (b.p. 245° C.), glycidol (b.p. 167° C.), triisobutylene oxide (b.p. 203° C.), vinyl cyclohexane dioxide (b.p. 227° C.), vinyl cyclohexene monoxide (b.p. 169° C.), limonene dioxide (b.p. 242° C.), allyl-9,10-epoxystearate (b.p. 282° C. at 50 mm), and epoxidized linseed oil. Epoxypropane, 1,2-epoxybutane and 3,4-epoxy-1-butene are representative of suitable low-boiling epoxides.

The epoxidized oils (e.g., epoxidized linseed oil or epoxidized soybean oil, available from the Swift Chemical Company as "Epoxol 9-5" and "Epoxol 7-4", respectively), may be prepared by the reaction of the oils with aqueous peracetic acid solutions, or with hydrogen peroxide and acetic acid in a manner well known to those skilled in the art. Characteristically, such epoxidized oils have an oxirane oxygen content of at least 3%, preferably 5 to 15%. They are reported to have been previously used or proposed for use in the art as scavengers for halogens or carboxylic or mineral acids.

In the second category, linseed, tung, perilla, soybean, fish and dehydrated castor oil are representative of suitable natural drying oils. Such drying oils are mixed triglycerides of mono- and polyethenoid fatty acids and desirably have a degree of unsaturation corresponding to a true iodine value of at least 120, preferably at least 170. Tung oil, raw linseed oil and boiled linseed oil are accordingly the preferred stabilizers among the natural drying oils. Synthetic esters of unsaturated acids and unsaturated liquid polymers derived from butadiene-1,3 are representative of synthetic drying oils that may be used as stabilizers in this invention.

The unsaturated fatty acids useful in this invention generally have from about 4 to about 30 carbon atoms, preferably from about 6 to about 22 carbon atoms per molecule. Such acids may be mono- or polyethenoid, branched or unbranched and may possess any one or more substituent groups, such as hydroxy, halogen, lower alkoxy, etc., characterized in that they do not substantially impair the stabilizing effect of the acids. Particularly useful fatty acids include oleic acid and linoleic acid. Other unsaturated acids that may be used include, among others, crotonic, isocrotonic, methacrylic, vinylacrylic, sorbic, undecylenic, myristoleic, ricinoleic (12-hydroxyoleic), linolenic, erucic and triacontenoic acids. Among these acids, those in the $C_{12}$ to $C_{22}$ range are commonly derived by hydrolysis and fractionation of vegetable, marine or land-animal fats and oils, where they usually occur as triglyceride esters. Others can be produced by various methods of chemical synthesis as is otherwise well known in the art.

Besides the triglycerides, other esters of such $C_4$ to $C_{30}$ unsaturated fatty acids may be used as stabilizers in this invention. Such other esters of these acids may be the mono- or diglycerides of the various unsaturated acids, e.g., glyceryl monooleate, or they may be alkyl esters produced by a base-catalyzed exchange reaction of a triglyceride with an alcohol or by a standard esterification reaction of the acid with the desired alcohol using procedures well-known to those of ordinary skill in the art. The alcohol used for this purpose may be a $C_1$ to $C_{12}$ alkanol e.g., methyl, ethyl, octyl or lauryl alcohol, or it may be an unsaturated alcohol such as allyl alcohol. Useful esters of this sort thus include, for instance, ethyl oleate, propyl oleate, butyl oleate, methyl tallowate, lauryl methacrylate, allyl oleate, methylated corn oil acids, methylated soya acids, methyl lardate, polyethylene glycol dioleate, and so on. Preferably such unsaturated esters have an iodine value of at least 20, most preferably between about 50 and 150.

Tung oil and the various forms of linseed oil are defined as follows:

Tung oil is a drying oil derived from the seeds of *Aleurites Cordata*, a tree indigenous to China and Japan, by roasting, grinding and pressing. The chief constituent of tung oil is eleostearic acid (80 percent), predominantly in the glyceride form.

Linseed oil is a drying oil derived from the seeds of the flax plant *Linum Usitatissimum* by subjecting the seeds to pressure or solvent extraction. The chief constituents of linseed oil are the glycerides of linolenic, oleic, linoleic and saturated fatty acids.

Raw linseed oil is linseed oil which has been filtered but otherwise untreated.

Boiled linseed oil is raw linseed oil which has been heated and then mixed with a catalytic amount of a drying agent such as an oxide of manganese, lead, or cobalt, or their naphthenates, resinates, or linoleates to accelerate drying.

In practicing this invention, the stabilizer is mixed with the pentachlorophenol in an amount effective to reduce degradation of the pentachlorophenol to the required degree. The amount of stabilizer employed will depend somewhat on the particular stabilizer or stabilizers selected and the kind and amount of impurities initially present in the pentachlorophenol or expected to be formed therein during its anticipated thermal treatment. However, typical effective stabilizing concentrations are in the range of from about 0.01 to about 1.0 percent, preferably from about 0.2 to about 0.5 percent, stabilizer relative to the total weight of the pentachlorophenol. The optimum concentration for any given case can be readily determined by preliminary routine tests. The stabilizer may be mixed with the pentachlorophenol either while the latter is in the molten state or while it is in the solid state to be melted later.

This invention is effective in reducing the degradation of pentachlorophenol due to adverse conditions, particularly when pentachlorophenol is required to be kept in the molten state by the application of heat thereto over an extended time. The invention is effective even when molten pentachlorophenol is maintained in contact with metals that are known to accelerate its degradation, e.g., stainless steel or Monel metal, and may also be effective in reducing degradation that is accelerated by exposure of pentachlorophenol to other factors including, but not limited to scale, rust, light, air, and chemical impurities.

When technical grade or impure pentachlorophenol is to be purified by distillation while making use of the present invention, a conventional reduced pressure still is satisfactory to carry out the distillation. For example, the distillation apparatus may be a vacuum batch still with heat being supplied to the still by a forced circulation reboiler heated with steam. Vapors pass out the top of the batch pot through a column containing side-to-side trays and are condensed in a shell- and tube-type condenser (vapor on the inside of the tubes and high pressure steam generated on the outside). A reduced pressure is maintained on the system by a dual stage jet ejector in a manner well known in the art.

Typically, the distillation is performed under vacuum conditions, e.g., at a pressure of from about 30 up to about 200 mm Hg, preferably from about 35 to about 150 mm Hg and at a temperature of from about 185° C. to 235° C., most preferably from about 195° C. to about 220° C. Distillation may be continued to achieve from about 84% to 93%, often from about 90% to 93%, distillate recovery with good results.

When impure pentachlorophenol containing a proper amount of stabilizer is distilled under the conditions noted above, the distillate comes over essentially water-white in color, while the residue remains as a dark liquid. That is, a 10 weight percent sample of the distillate in xylene generally yields a transmission value using a light having a wavelength of 475 millimicrons and a light path of 10 mm of from about 95% to about 100% of the value of a water-white xylene reference standard. The chlorodioxins content of the essentially water-white colored distillate is generally below about 25 p.p.m.

The hot, liquid, purified pentachlorophenol distillate, which depending upon the boiling point of the stabilizer employed may or may not contain an effective concentration of the stabilizer that was previously added to inhibit degradation during distillation, may be then processed into solid form such as prills, pellets, or blocks. If a relatively high-boiling stabilizer is used to prevent degradation during the distillation step, it may be advantageous to add additional amounts of the same or a different stabilizer to the liquid pentachlorophenol distillate prior to processing into solid form, particularly if the pentachlorophenol distillate is to be maintained in the molten state for a substantial period, or is allowed to solidify only to be later heated and remelted.

The invention is additionally illustrated in connection with the following illustrative examples. It should be understood, however, that the invention is not limited to the specific details described.

DISTILLATION OF TECHNICAL GRADE PENTACHLOROPHENOL

In order to simulate the environment to which the pentachlorophenol would be subjected during the course of distillation in actual purification processes, samples of technical grade pentachlorophenol are loaded into an apparatus designed to permit the maintenance of controlled conditions. This apparatus consists of a hot plate onto which is mounted an insulated aluminum block for the conduction of heat, having nine holes into which glass sample tubes are inserted, containing the pentachlorophenol samples to be tested. A sample tube has an elongated form, so that its upper end serves as an air condenser. An opening is provided at the top of the tube and is packed with glass wool. The temperature of the aluminum block is constantly controlled using a YSI Thermistemp Model 63 RC temperature controller, whose probe is inserted in the aluminum block. In conducting each test, technical grade pentachlorophenol (20 grams), and the stabilizer (0.1 gram), if any, are heated in a sample tube to 450° F. (232° C.) and maintained at this temperature for 16 hours. Nine experiments may be run simultaneously. Simulation of exposure of the pentachlorophenol to stainless steel or Monel metal surfaces is carried out by inserting a ½" diameter by 2" long stainless steel or Monel metal open-ended tube into the glass sample tube with the pentachlorophenol and the stabilizer.

Total chlorophenols were determined at the end of each test by titration of a weighed sample with standard base and calculated as pentachlorophenol.

Octachlorodibenzo-p-dioxin was determined by dissolving the pentachlorophenol sample in aqueous sodium hydroxide, extracting the caustic insolubles with pesticide grade hexane, passing the hexane solution through a column packed with alumina in order to remove interfering constituents, and determining octachlorodibenzo-p-dioxin quantitatively in the hexane solution with a gas chromatograph using an electron capture detector by comparison with an authentic standard.

EXAMPLE 1

Control Test

A sample of technical grade pentachlorophenol (20 g) is melted in a glass tube in the heating apparatus at 450° F. (232° C.) and held at this temperature for 16 hours in the absence of any stabilizer. Prior to this heat treatment, the total chlorophenols content of the sample is 96.10 weight percent and the octachlorodibenzo-p-dioxin content is 2,769 p.p.m. After the heat treatment is completed, the total chlorophenols content of the sample is 91.53 weight percent and the octachlorodibenzo-p-dioxin content is 37,100 p.p.m.

Stabilizer: Epoxidized Linseed Oil

A 20 g sample of the same technical grade pentachlorophenol as was used in the control test is melted in a glass tube in the heating apparatus at 232° C. in intimate admixture with 0.1 g of Epoxol 9-5 (epoxidized linseed oil). The sample is held at this temperature for 16 hours. Prior to this heat treatment the total chlorophenols content of the sample is 96.10 weight percent and the octachlorodibenzo-p-dioxin content is 2,769 p.p.m. After the heat treatment is completed, the total chlorophenols content of the sample is 95.93 weight percent (as against 96.10 weight percent initially) and the octachlorodibenzo-p-dioxin content is 1,394 p.p.m.

Thus, the chlorodioxin content was actually reduced by about 50% in the course of the heat treatment when the pentachlorophenol was stabilized in accordance with this invention whereas the chlorodioxin content increased by a factor of about 13.5 when the heat treatment was conducted in the absence of any stabilizer under otherwise comparable conditions.

EXAMPLE 2

Control Test

A sample of technical grade pentachlorophenol (20 g) is melted in a glass tube in the heating apparatus at 232° C. in the presence of a stainless steel tube having the aforementioned standard dimensions. The sample is held at this temperature for 16 hours in the absence of any stabilizer. As in Example 1, the total chlorophenols content of this sample prior to heat treatment is 96.10 weight percent; and the octachlorodibenzo-p-dioxin content is 2,769 p.p.m.; after the heat treatment is completed, the total chlorophenols content of the sample is only 81.31 weight percent.

Stabilizer: Raw Linseed Oil

A 20 g sample of the same technical grade pentachlorophenol as in the control test is melted in a glass tube in the heating apparatus at 232° C. in intimate admixture with 0.1 g of raw linseed oil. A stainless steel tube having the aforementioned standard dimensions is placed in the glass tube and the sample is held at 232° C. for 16 hours as in the control test. After the heat treatment is completed, the total chlorophenols content of the sample is 95.12 weight percent (as against 96.10 weight percent initially) and the octachlorodibenzo-p-dioxin content is 2,237 p.p.m. (as against 2,769 p.p.m. initially).

Again, an actual net reduction in chlorodioxin content was obtained during the heat treatment, even in the presence of stainless steel, when the chlorophenol was stabilized in accordance with this invention. By contrast, very severe degradation took place when unstabilized pentachlorophenol was heated under otherwise identical conditions.

EXAMPLE 3

Control Test

A 20 g sample of the same technical grade pentachlorophenol as in Example 1 is melted in a glass tube in the heating apparatus at 232° C. in the presence of a Monel metal tube having the aforementioned standard dimensions. The sample is held at this temperature for 16 hours in the absence of any stabilizer. After the heat treatment is completed, the total chlorophenols content of the sample is 77.60 weight percent (as against 96.10 weight percent initially).

Stabilizer: Tung Oil

A sample of the same technical grade pentachlorophenol as in Example 1 is melted in a glass tube in the heating apparatus at 232° C. in intimate admixture with 0.1 g of tung oil. A Monel metal tube having the aforementioned standard dimensions is placed in the glass tube and the sample is held at 232° C. for 16 hours. After the heat treatment is completed, the total chlorophenols content of the sample is 95.38 weight percent (as against 96.10 weight percent initially).

Again, in comparison with the control test, it is seen that relatively little degradation occurs in the case of pentachlorophenol that has been stabilized in accordance with this invention when it is kept molten in contact with Monel metal, but very severe degradation takes place when molten pentachlorophenol is kept in contact with Monel metal without any stabilizer.

EXAMPLE 4

Various other materials have been tested for their effectiveness as stabilizers when added to technical grade pentachlorophenol that is maintained molten or is to be distilled.

A summary of the results obtained is presented below in Table I. In each case, a 20 g sample of technical grade pentachlorophenol is heated in admixture with 0.1 g of the selected stabilizer, if any, at 232° C. for 16 hours in glass. The technical grade pentachlorophenol initially contains 96.10% pentachlorophenol and 2,769 p.p.m. of octachlorodibenzo-p-dioxin. Some results of heating in the additional presence of stainless steel or Monel metal are also given.

TABLE I
STABILITY TESTS WITH TECHNICAL PENTACHLOROPHENOL

A. Pentachlorophenol Tested in Glass

| Stabilizer | Pentachlorophenol, Wt. Percent | Octachlorodibenzo-p-dioxin, p.p.m. |
|---|---|---|
| None (Initial comp.) | 96.10 | 2,769 |
| After Heating | | |
| None | 91.53 | 37,100 |
| Epoxol 9-5 | 95.93 | 1,394 |
| Phenylglycidyl ether | 95.38 | — |
| Tung oil | 95.34 | — |
| Oleic acid | 95.33 | — |
| Linoleic acid | 95.28 | — |
| Raw linseed oil | 95.15 | 2,212 |
| Boiled linseed oil | 94.18 | — |

B. Pentachlorophenol Tested in Glass With A Stainless Steel Tube

| Stabilizer | Pentachlorophenol, Wt. Percent | Octachlorodibenzo-p-dioxin, p.p.m. |
|---|---|---|
| None (Initial Comp.) | 96.10 | 2,769 |
| After Heating | | |
| None | 81.31 | — |
| Tung oil | 95.50 | — |
| Raw linseed oil | 95.12 | 2,237 |
| Epoxol 9-5 | 94.65 | — |
| Conjugated oil (122-G) - PVO International, Inc. | 94.15 | — |

C. Pentachlorophenol Tested in Glass With A Monel Metal Tube

| Stabilizer | Pentachlorophenol, Wt. Percent | Octachlorodibenzo-p-dioxin, p.p.m. |
|---|---|---|
| None (Initial Comp.) | 96.10 | 2,769 |
| After Heating | | |
| None | 76.60 | — |
| Tung oil | 95.38 | — |
| Epoxol 9-5 | 94.73 | — |

Another set of tests was conducted to illustrate the effectiveness of various materials as stabilizers in preventing the thermal degradation of purified pentachlorophenol, i.e. pentachlorophenol that has been refined by distillation or other conventional purification processes, e.g., crystallization.

EXAMPLE 5

Control

A 20 g sample of purified pentachlorophenol is melted in a glass tube in the heating apparatus at 400° F. (204° C.) and held at this temperature for 16 hours in the absence of any stabilizer. Prior to this heat treatment the total chlorophenols content of the purified sample is 100.36 weight percent (calculated as pentachlorophenol) and the octachlorodibenzo-p-dioxin content, is 27 p.p.m. After the 16-hour treatment, the total chlorophenols content of the sample is 98.91 weight percent and the octachlorodibenzo-p-dioxin content, is 5,872 p.p.m.

Stabilizer: Epoxidized Linseed Oil

A 20 g sample of the same purified pentachlorophenol as was used in the control is melted in a glass tube in the heating apparatus at 204° C. in intimate admixture with 0.1 g of epoxidized linseed oil (Epoxol 9-5). The sample is held at this temperature for 16 hours.

After the heat treatment is completed, the total chlorophenols content of the sample is 100.03 weight percent (as against 100.36% initially) and the octachlorodibenzo-p-dioxin content, is 50 p.p.m. (as against 27 p.p.m. initially). Excellent stabilization has thus been achieved.

EXAMPLE 6

Control

A 20 g sample of the same purified pentachlorophenol as was used in Example 5 is melted in a glass tube in the heating apparatus at 204° C. in the presence of a stainless steel tube having the aforementioned standard dimensions. The sample is held at this temperature for 16 hours in the absence of any stabilizer.

After the 16-hour heat treatment is completed, the total chlorophenols content of the sample is 98.02 weight percent and the octachlorodibenzo-p-dioxin content, is 4,293 p.p.m.

Stabilizer: Epoxidized Linseed Oil

A 20 g sample of the same purified pentachlorophenol as was used in Example 5 is melted in a glass tube in the heating apparatus in intimate admixture with 0.1 g of epoxidized linseed oil (Epoxol 9-5) in the presence of a stainless steel tube having the aforementioned standard dimensions. The sample is held at 204° C. for 16 hours.

After this heat treatment is completed, the total chlorophenols content of the sample is 100.30 weight percent (as against 100.36% initially) and the octachlorodibenzo-p-dioxin content is 12 p.p.m. (as against 27 p.p.m. initially). Again, it is seen that epoxidized linseed oil provides excellent protection against thermal degradation even in the presence of stainless steel.

EXAMPLE 7

Control

A 20 g sample of the same purified pentachlorophenol as was used in Example 5 is melted in a glass tube in the heating apparatus at 204° C. in the presence of a Monel metal tube having the aforementioned standard dimensions. The sample is held at this temperature for 16 hours in the absence of any stabilizers.

After this heat treatment is completed, the total chlorophenols content of the sample is 98.78 weight percent and the octachlorodibenzo-p-dioxin content is 5,541 p.p.m.

Stabilizer: Epoxidized Linseed Oil

A 20 g sample of the same purified pentachlorophenol as was used in Example 5 is melted in a glass tube in the heating apparatus in intimate admixture with 0.1 g of epoxidized linseed oil (Epoxol 9-5) in the presence of a Monel metal tube having the aforementioned standard dimensions. The sample is held at 204° C. for 16 hours. After this heat treatment is completed, the total chlorophenols content of the sample is 99.82 weight percent (as against 100.36% initially) and the octachlorodibenzo-p-dioxin content is 12 p.p.m. (as against 27 p.p.m. initially). Outstanding protection against thermal degradation is seen to have been obtained not only in terms of keeping any loss of pentachlorophenol to a minimum, but particularly also in preventing the formation of any noxious chlorodioxin.

EXAMPLE 8

Another set of tests was conducted to demonstrate the effectiveness of various materials as stabilizers capable of protecting purified pentachlorophenol against thermal degradation when it is maintained in the molten state or is to be heated to melt.

In each case, a 20 g sample of the same purified pentachlorophenol as was described above in Example 5 (100.36% $C_6Cl_5OH$; 27 p.p.m. chlorodioxin) is heated in the presence of 0.1 g of the selected stabilizer at 204° C. for 16 hours in glass.

A summary of the results is presented in Table II below. Results of heating purified pentachlorophenol in the presence of a tube of either stainless steel or Monel metal are also included.

TABLE II
STABILITY TESTS WITH PURIFIED PENTACHLOROPHENOL

A. Pentachlorophenol Tested In Glass

| Stabilizer | Total Phenols By Titration, Wt. % | Octa-chlorodibenzo-p-dioxin, p.p.m. |
|---|---|---|
| None (Initial Comp.) After Heating | 100.36 | 27 |
| None | 98.91 | 5,872 |
| Raw linseed oil | 100.34 | — |
| Tung oil | 100.11 | — |
| Epoxol 9-5 | 100.03 | 50 |

B. Pentachlorophenol Tested In Glass With A Stainless Steel Tube

| Stabilizer | Total Phenols By Titration, Wt. % | Octa-chlorodibenzo-p-dioxin, p.p.m. |
|---|---|---|
| None (Initial Comp.) After Heating | 100.36 | 27 |
| None | 98.02 | 4,293 |
| Raw linseed oil | 100.10 | — |
| Tung oil | 100.10 | — |
| Epoxol 9-5 | 100.30 | 12 |

C. Pentachlorophenol Tested In Glass With A Monel Metal Tube

| Stabilizer | Total Phenols By Titration, Wt. % | Octa-chlorodibenzo-p-dioxin, p.p.m. |
|---|---|---|
| None (Initial Comp.) After Heating | 100.36 | 27 |
| None | 98.78 | 5,541 |
| Raw linseed oil | 100.20 | — |
| Tung oil | 100.06 | — |
| Epoxol 9-5 | 99.82 | 12 |

EXAMPLE 9

It is well known that technical pentachlorophenol often contains some dissolved hydrogen chloride which would be released when the pentachlorophenol is melted or distilled. In addition, if any decomposition of the chlorinated phenol takes place during distillation, some HCl is likely to be evolved. In view of this, a series of runs was made using 0.5% of epoxidized linseed oil (Epoxol 9-5) or raw linseed oil, respectively, based on the weight of the pentachlorophenol, to which HCL was also added in order to determine if the stabilizers would be effective in the presence of HCl.

These runs were conducted in the same manner as described earlier herein, heating the pentachlorophenol sample at 232° C. for 16 hours, except that in Runs 5, 6 and 7 the molten sample was substantially saturated with HCl by bubbling anhydrous HCl at a rate of about 0.3 g mole/hour through the 20 g sample of pentachlorophenol during the entire heating period in these runs.

A summary of the results obtained is presented in Table III below.

TABLE III
Effect of HCl on Heat Stability of Technical Pentachlorophenol

| Run | Stabilizer | HCl | Stainless Steel | Monel Metal | Total Chlorophenol By Titration, Wt. % | Octochlorodibenzo-Dioxin p.p.m |
|---|---|---|---|---|---|---|
| 1 (*Blank) | None | None | No | No | 96.10 | 2,769* |
| 2 (Control) | None | None | No | No | 91.53 | 37,100 |
| 3 (Control) | None | None | No | Yes | 77.60 | — |
| 4 (Control) | None | None | Yes | No | 81.31 | — |
| 5 | None | Yes | No | Yes | 91.12 | — |
| 6 | Epoxol 9-5 | Yes | No | Yes | 95.15 | 1,745 |
| 7 | Raw Linseed Oil | Yes | Yes | No | 94.37 | 2,201 |

*Initial Technical Pentachlorophenol, unheated.

Comparison of Run 5 (91.12%) with Run 3 (77.60%), each run without any added stabilizer, indicates that HCl is not detrimental to the stability of pentachlorophenol and, in fact, may improve it. Runs 6 and 7 further demonstrate that HCl does not interfere with the ability of the added chemical stabilizers to protect the chlorinated phenol against chemical degradation.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the scope or spirit of the invention claimed.

What is claimed is:

1. Chlorinated phenol containing at least one stabilizer selected from the group consisting of $C_4$ to $C_{30}$ unsaturated fatty acids, esters of said fatty acids, and epoxides.

2. Chlorinated phenol according to claim 1 wherein the stabilizer comprises a $C_6$ to $C_{20}$ unsaturated fatty acid.

3. Chlorinated phenol according to claim 1 wherein the stabilizer comprises a triglyceride of a $C_6$ to $C_{20}$ unsaturated fatty acid.

4. Chlorinated phenol according to claim 1 wherein the stabilizer comprises a drying oil.

5. Chlorinated phenol according to claim 1 wherein the stabilizer is an ester of a $C_4$ to $C_{30}$ unsaturated fatty acid esterified with an alcohol selected from the group consisting of $C_1$ to $C_{12}$ alkanol and allyl alcohol.

6. Chlorinated phenol according to claim 1 wherein the stabilizer is an epoxide having a boiling point above 150° C.

7. Pentachlorophenol containing in admixture therewith a stabilizing amount of at least one member of the group consisting of $C_4$ to $C_{30}$ unsaturated fatty acids, esters of said fatty acids, and epoxides.

8. Pentachlorophenol according to claim 7 containing from 0.01 to 1 percent by weight of a drying oil.

9. Pentachlorophenol according to claim 7 containing about 0.2 to about 0.5 percent by weight of a member of the group consisting of tung oil, linseed oil, epoxidized linseed oil and mixtures thereof.

10. Pentachlorophenol according to claim 7 containing about 0.2 to about 0.5 percent by weight of a member selected from the group consisting of glycidol, phenylglycidyl ether, triisobutylene oxide, vinylcyclohexane monoxide, vinylcyclohexene dioxide, limonene oxide, allyl-9,10-epoxystearate, and mixtures thereof.

11. A process for inhibiting the formation of chlorinated dibenzo-p-dioxin in molten pentachlorophenol which comprises adding to the pentachlorophenol about 0.01 to about 1 percent, based on the weight of the weight of pentachlorophenol, of at least one stabilizer selected from the group consisting of $C_4$ to $C_{30}$ unsaturated fatty acids, esters of said fatty acids, and epoxides having a boiling point of at least 150° C.

12. A process according to claim 11 wherein the stabilizer comprises linseed oil or epoxidized linseed oil.

13. In a process wherein pentachlorophenol is maintained at a temperature above its melting point, the improvement which comprises admixing with the pentachlorophenol 0.01 to 1.0 percent, based on the weight of pentachlorophenol, of at least one stabilizer selected from the group consisting of $C_4$ to $C_{30}$ unsaturated fatty acids, esters of said fatty acids, and epoxides having an atmospheric boiling point of at least 190° C.

14. A process according to claim 13 wherein the pentachlorophenol is maintained above its melting point in contact with a metal.

15. A process according to claim 13 wherein the stabilizer is selected from the group consisting of oleic acid, linoleic acid, linseed oil, epoxidized linseed oil, phenylglycidyl ether and mixtures thereof.

16. A process according to claim 13 wherein the molten pentachlorophenol further contains hydrogen chloride.

17. In a process wherein pentachlorophenol is purified by distillation, the improvement which comprises adding to the pentachlorophenol to be distilled about 0.01 to 1.0 percent, based on the weight of pentachlorophenol, of a stabilizer selected from the group consisting of $C_4$ to $C_{30}$ unsaturated fatty acids, esters of such fatty acids, and epoxides.

18. A process according to claim 17 wherein the stabilizer is selected from the group consisting of linseed oil and epoxidized linseed oil and is added to the pentachlorophenol in a concentration of between about 0.2 and about 0.5 percent.

19. A process according to claim 18 wherein the pentachlorophenol is in contact with stainless steel.

20. A process according to claim 18 wherein the pentachlorophenol is in contact with monel.

* * * * *